(12) United States Patent
Tomita

(10) Patent No.: US 7,091,206 B2
(45) Date of Patent: Aug. 15, 2006

(54) PROCESS FOR PRODUCING PYRIMIDINE DERIVATIVE AND INTERMEDIATE THEREOF

(75) Inventor: Toshio Tomita, Kusatsu (JP)

(73) Assignee: Nippon Shinyaku Co., LTD, (JP)

( * ) Notice: Subject to any disclaimer, the term of this patent is extended or adjusted under 35 U.S.C. 154(b) by 338 days.

(21) Appl. No.: 10/363,232

(22) PCT Filed: Sep. 7, 2001

(86) PCT No.: PCT/JP01/07767

§ 371 (c)(1),
(2), (4) Date: Jun. 6, 2003

(87) PCT Pub. No.: WO02/20494

PCT Pub. Date: Mar. 14, 2002

(65) Prior Publication Data

US 2004/0023985 A1    Feb. 5, 2004

(51) Int. Cl.
*C07D 239/42* (2006.01)
(52) U.S. Cl. ...................... 514/256; 544/242
(58) Field of Classification Search ............... 544/249, 544/242; 514/256
See application file for complete search history.

(56) References Cited

U.S. PATENT DOCUMENTS 5,945,426 A * 8/1999 Chokai et al. ............... 514/269

6,191,149 B1   2/2001  Chokai et al. ............... 514/351

OTHER PUBLICATIONS

"Na+ and high-voltage activated Ca2+ channel blocking actions of NS-7, a novel neuroprotective agent, in NG108-15 cells." Suma et al. European Journal of Pharmacology 336 (1997) pp. 283-290.*

* cited by examiner

*Primary Examiner*—Deepak Rao
*Assistant Examiner*—Jason H. Johnsen
(74) *Attorney, Agent, or Firm*—Greenberg Traurig LLP

(57) ABSTRACT

The present invention relates to a method for producing a pyrimidine derivate useful as a neurocyte neurocyte necrosis inhibitor and an intermediate thereof. Disclosed is a method for producing an acid salt of 4-(4-fluorophenyl)-2-methyl-6-(5-piperidinopentyloxy) pyrimidine. The method comprises reacting 4-chloro-6-(4-fluorophenyl)-2-methylpyrimidine with 5-piperidino-1-pentanol, hydrating the thus obtained 4-(4-fluorophenyl)-2-mehtyl-6-(5-piperidinopentylox) pyrimidine and then converting the resultant hydrate into an acid salt. The hydrate as a describe above; and a method for producing the hydrate is part of this invention. According to the present invention, a highly pure acid salt of 4-(4-fluorophenyl)-2-methyl-6-(5-piperidinopentyloxy) pyrimidine can be readily and efficiently produced without using a column chromatography. Thus, this method is suitable for the production thereof on a industrial scale.

14 Claims, 1 Drawing Sheet

US 7,091,206 B2

PROCESS FOR PRODUCING PYRIMIDINE DERIVATIVE AND INTERMEDIATE THEREOF

TECHNICAL FIELD

The present invention relates to a method for producing a pyrimidine derivative which is an extremely excellent neurocyte necrosis inhibitor, i.e., an acid salt of 4-(4-fluorophenyl)-2-methyl-6-(5-piperidinopentyloxy)pyrimidine, as well as an intermediate thereof.

BACKGROUND ART 4-(4-Fluorophenyl)-2-methyl-6-(5-piperidinopentyloxy) pyrimidine hydrochloride (hereinafter referred to as Compound A) is known to have a neurocyte necrosis inhibiting effect and thus to be useful as a medical drug (International Publication WO96/07641).

In a known method for producing Compound A (see Example 1 in the above-mentioned publication), because of oily characteristic and resulting difficulty in crystallization of 4-(4-fluorophenyl)-2-methyl-6-(5-piperidinopentyloxy) pyrimidine (free base of Compound A, hereinafter referred to as Compound 1) obtained by a reaction between the starting materials, 4-chloro-6-(4-fluorophenyl)-2-methylpyrimidine and 5-piperidino-1-pentanol, a column chromatography was employed to isolate and purify Compound 1, which is then converted into a hydrochloride, whereby obtaining Compound A. However, such isolation and purification by the column chromatography does not enable a large scale production of Compound A at a high purity, and is not suitable for an industrial manufacturing process. Accordingly, it has been demanded to develop an efficient method for obtaining a highly pure Compound A industrially at a high yield by a simple convenient procedure without employing a column chromatography.

SUMMARY OF THE INVENTION

An objective of the invention is to provide a method for producing a highly pure Compound A at a high yield which employs no column chromatography and is suitable for a mass production and also to provide an intermediate useful for such a production as well as a method for producing the same.

The inventors made an effort and finally discovered, in the course of investigating a method for producing Compound A, that by stirring Compound 1 isolated or a Compound 1-containing reaction solution in the presence of water a hydrate of Compound 1 can be obtained, that this hydrate readily crystallizes under a suitable condition, and that by using this hydrate Compound A can be obtained efficiently at a high purity (about 99.9%), whereby establishing the present invention.

The present invention is characterized in that Compound 1 is obtained as a hydrate, preferably as a crystalline hydrate and that this hydrate is used for producing Compound A.

Compound 1 is almost insoluble in water, and is soluble in organic solvents (e.g., cyclohexane, toluene, ethyl acetate, diisopropyl ether, t-butylmethyl ether, methanol, ethanol, isopropanol, acetonitrile, acetone, tetrahydrofuran, N,N-dimethylformamide).

The present invention is (a) a method for producing a highly pure acid salt of 4-(4-fluorophenyl)-2-methyl-6-(5-piperidinopentyloxy)pyrimidine comprising forming a hydrate of 4-(4-fluorophenyl)-2-methyl-6-(5-piperidinopentyloxy)pyrimidine followed by a conversion into the acid salt and (b) a hydrate of 4-(4-fluorophenyl)-2-methyl-6-(5-piperidinopentyloxy)pyrimidine produced as an intermediate in the method described above in (a), and (c) a method for producing a hydrate of 4-(4-fluorophenyl)-2-methyl-6-(5-piperidinopentyloxy)pyrimidine.

More particularly, the present invention is:
(1) a method for producing an acid salt of 4-(4fluorophenyl)-2-methyl-6-(5-piperidinopentyloxy)pyrimidine comprising forming a hydrate of 4-(4-fluorophenyl)-2-methyl-6-(5-piperidinopentyloxy)pyrimidine (Compound 1) and then converting into an acid salt;
(2) a production method according to the above-mentioned (1) wherein the hydrate is a hemihydrate;
(3) a production method according to the above-mentioned (1) wherein the hydrate is a crystalline hemihydrate;
(4) a production method according to the above-mentioned (1) wherein the acid salt is a hydrochloride;
(5) a production method according to the above-mentioned (1) wherein the acid salt is formed after isolating the hydrate;
(6) a hydrate of 4-(4-fluorophenyl)-2-methyl-6-(5-piperidinopentyloxy)pyrimidine (Compound 1);
(7) a hydrate according to the above-mentioned (6) wherein the hydrate is a hemihydrate;
(8) a hydrate according to the above-mentioned (6) wherein the hydrate is a crystalline hemihydrate;
(9) a method for producing a hydrate of 4-(4-fluorophenyl)-2-methyl-6-(5-piperidinopentyloxy)pyrimidine comprising dissolving 4-(4-fluorophenyl)-2-methyl-6-(5-piperidinopentyloxy)pyrimidine (Compound 1) in an acidic aqueous solution and adjusting the solution at pH 7 or higher with a basic aqueous solution;
(10) a method for producing a hydrate of 4-(4-fluorophenyl)-2-methyl-6-(5-piperidinopentyloxy)pyrimidine comprising dissolving 4-(4-fluorophenyl)-2-methyl-6-(5-piperidinopentyloxy)pyrimidine (Compound 1) in an organic solvent and distilling the solvent off in the presence of water followed by cooling;
(11) a method for producing a hydrate of 4-(4-fluorophenyl)-2-methyl-6-(5-piperidinopentyloxy)pyrimidine comprising stirring 4-(4-fluorophenyl)-2-methyl-6-(5-piperidinopentyloxy)pyrimidine (Compound 1) together with water or an aqueous organic solvent;
(12) a production method according to the above-mentioned (9) to (11) wherein the hydrate is a hemihydrate;
(13) a production method according to the above-mentioned (9) to (11) wherein the hydrate is a crystalline hemihydrate;
(14) a method for purifying a hydrate of 4-(4-fluorophenyl)-2-methyl-6-(5-piperidinopentyloxy)pyrimidine comprising adding water to a solution of a hydrate obtained by a method according to the above-mentioned (9) or (10) dissolved in an aqueous organic solvent; and,
(15) a purification method according to the above-mentioned (14) wherein the aqueous organic solvent is a solvent mixture of water and acetone.

A hydrate of Compound 1 (hereinafter referred to as an inventive hydrate) is a novel compound which has not been reported, and is useful as an intermediate in the process of the production of Compound A. Since the inventive hydrate can be purified more readily when it is crystallized and can be imparted with a further higher purity, it is an excellent intermediate for the mass production of Compound A.

The present invention is further detailed below.

A "hydrate" in the invention may for example be an amorphous or crystalline solid containing a certain ratio of water. A preferred hydrate is a "hemihydrate", and a crystalline hydrate is especially preferred.

An "acid salt" may for example be a salt of an inorganic acid such as hydrochloric acid, sulfuric acid, nitric acid, phosphoric acid, hydrofluoric acid, hydrobromic acid and the like, or a salt of an organic acid such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid and the like. Among those listed above, a hydrochloride is preferred.

An "organic solvent" may be any of the organic solvents in which Compound 1 is soluble. Those which can be exemplified are hydrocarbon-based solvents such as cyclohexane, toluene, benzene and hexane, ester-based solvents such as ethyl acetate, ether-based solvents such as diethyl ether, t-butylmethyl ether and diisopropyl ether, alcohols such as methanol and ethanol, ketones such as acetone, methyl ethyl ketone, diisobutyl ketone and methyl isobutyl ketone as well as a water-soluble solvent such as acetonitrile and tetrahydrofuran. Among those listed above, cyclohexane is especially preferred.

An "aqueous organic solvent" means a solvent mixture of a water-miscible organic solvent and water. Such a water-miscible organic solvent may for example be a water-soluble lower alcohol such as methanol, ethanol, propyl alcohol, isopropyl alcohol and t-butanol, glycols such as ethylene glycol and propylene glycol, ketones such as acetone, methyl ethyl ketone, diisobutyl ketone and methyl isobutyl ketone as well as water-soluble solvents such as acetonitrile, N,N-dimethylformamide (DMF), dimethyl sulfoxide (DMSO) and tetrahydrofuran. Any of these aqueous organic solvents may be employed alone or in combination with each other. Among those listed above, aqueous acetone is preferred.

An "acidic aqueous solution" may for example be an aqueous solution of an inorganic acid such as hydrochloric acid, sulfuric acid, hydrobromic acid and phosphoric acid and an organic acid such as acetic acid and formic acid. The amount of an acid may be any amount which is sufficient to convert Compound 1 as a free base into a salt.

A base in a "basic aqueous solution" may for example be a hydroxide of an alkaline metal (for example, sodium hydroxide, potassium hydroxide), a hydroxide of an alkaline earth metal (for example, calcium hydroxide), a carbonate of an alkaline metal (for example, sodium carbonate, potassium carbonate, sodium hydrogen carbonate, potassium hydrogen carbonate) as well as an aqueous solution of amines such as ammonia, pyridine and trimethylamine.

4-(4-Fluorophenyl)-2-methyl-6-(5-piperidinopentyloxy) pyrimidine (Compound 1) in the present invention means not only be Compound 1 itself but also an oil obtained by reacting 4-chloro-6-(4-fluorophenyl)-2-methylpyrimidine and 5-piperidino-1-pentanol in accordance with a known method as described above, an organic layer or oil described in the following Examples, or a reaction solution containing Compound 1, unless otherwise specified.

The present invention can be practiced as described below.

A method for producing an acid salt of Compound 1 which is one aspect of the present invention can be practiced by forming a hydrate of 4-(4-fluorophenyl)-2-methyl-6-(5-piperidinopentyloxy)pyrimidine as described below followed by a conversion into the acid salt of Compound 1 (for example, Compound A as a hydrochloride) in accordance with International Publication WO96/07641 or as directed in Example 5 described below.

An inventive hydrate can be formed for example by Production method 1, Production method 2 or Production method 3 in the following description.

A reaction product employed in these Production methods means an oil obtained by reacting 4-chloro-6-(4-fluorophenyl)-2-methylpyrimidine and 5-piperidino-1-pentanol in accordance with a known method as described above, an organic layer or oil described in the following Examples, or a reaction solution containing Compound 1, unless otherwise specified.

Production Method 1

Compound 1 as a reaction product is dissolved directly in an acidic aqueous solution, and adjusted at a neutral to basic pH (pH 7 or higher, i.e., pH 7 to pH 14) with a basic aqueous solution. The amount of the acidic aqueous solution is an amount sufficient to dissolve Compound 1. The amount of the base is an amount sufficient to convert the salt of Compound 1 back into a free base. The temperature for forming a hydrate is usually 0° C. to 80° C., preferably 10° C. to 50° C., more preferably around the ambient temperature at the site where the process is practiced (usually 10° C. to 35° C.).

Production Method 2

Compound 1 as a reaction product is dissolved in an organic solvent, and the solution is distilled in the presence of water to evaporate the solvent off and then cooled. The organic solvent is used in an amount sufficient to dissolve Compound 1. While the amount of water to be added may vary depending on the concentration of Compound 1 or the type of the solvent employed, it is an amount sufficient for forming the hydrate and precipitating the crystal. The temperature for forming a hydrate is usually 0° C. to 80° C., preferably 10° C. to 50° C., more preferably around the ambient temperature at the site where the process is practiced (usually 10° C. to 35° C.). The temperature for evaporating the solvent off is usually the boiling point of the solvent employed (e.g., about 30° C. to about 110° C.) or below.

Production Method 3

Compound 1 as a reaction product is stirred together with water or an aqueous organic solvent. More particularly, Compound 1 as an oil is stirred in water or an aqueous organic solvent. Among them, an aqueous acetone is preferable. The amount of water to be added is an amount sufficient for forming the hydrate and precipitating the crystal. While the ratio between an aqueous organic solvent and water may be selected appropriately based on the concentration of Compound 1 and the type of the aqueous organic solvent, the ratio (V/V) of water in the aqueous organic solvent is preferably 20% to 90%. For example, when acetone is employed, the ratio between water and acetone is preferably 4:7. When the treatment employs a solvent system in which the ratio of water to an aqueous organic solvent is low and a target substance is highly soluble, the yield can be increased finally by means of a dilution with water to precipitate the target substance. For forming a hydrate, stirring is continued for 10 minutes to 20 hours at a temperature usually of 0° C. to 80° C., preferably 10° C. to 50° C., more preferably around the ambient temperature at the site where the process is practiced (usually 10° C. to 35° C.).

Production methods 1, 2 and 3 may appropriately be combined. Preferably, Production method 1 or Production method 2 is conducted and then Production method 3 is conducted for the purification. For example, 4-chloro-6-(4- fluorophenyl)-2-methylpyrimidine and 5-piperidino-1-pentanol are reacted and then the solvent is distilled off if necessary to obtain a reaction product, which is then treated in accordance with Production method 1 or Production method 2 to obtain Compound 1 first as a hydrate, and then this crude hydrate is treated as described in Production method 3 to form a hydrate again for purification, whereby obtaining an extremely pure hydrate. The hydrate thus obtained may readily crystallize. Such a crystallization may be conducted under any non-limiting conditions (for example, cooling rate or stirring rate). The precipitated crystal is recovered by filtration and then recrystallized if necessary, whereby accomplishing the purification and isolation of a hydrate having a further higher purity. If necessary, the crystal can be dried. When a crystal obtained as described above is dried at 40° C., a hemihydrate is obtained usually. This crystal has the property to release the crystal water at a temperature of 40° C. or higher.

The production methods described above can be applied also to Compound 1 which has been isolated.

A hydrate of Compound 1 thus obtained can be identified as a hydrate by means of an elemental analysis, NMR spectroscopy and the like. A crystalline hydrate of Compound 1 can be identified to have a crystallinity microscopically or by means of a powder X-ray diffraction.

BEST MODE FOR CARRYING OUT THE INVENTION

Figure 1:
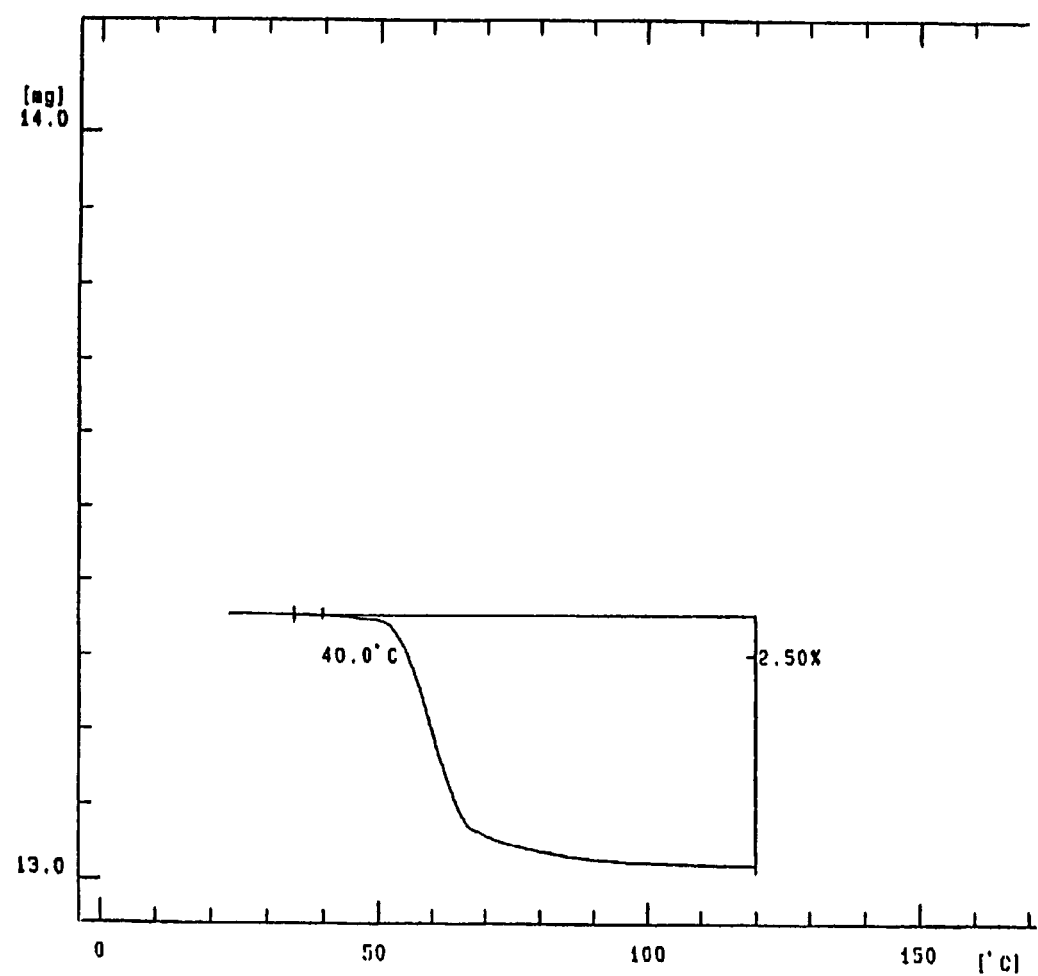
FIG. 1 shows a TG (thermogravimetry) chart of an inventive hydrate obtained in Example 1. The abscissa represents the measurement temperature, while the ordinate represents the change in weight.

The invention is further detailed in the following Examples, which are not intended to restrict the invention. A % water was measured by Karl Fischer method. A % thermogravimetric (TG) reduction was calculated by measuring the reduction in weight when the temperature was raised by 3° C. per minute using a thermogravimeter. A purity was measured by a high performance liquid chromatography (HPLC method).

REFERENCE EXAMPLE 1

Production of 4-(4-fluorophenyl)-2-methyl-6-(5-piperidinopentyloxy)pyrimidine

Production of 4-(4-fluorophenyl)-6-hydroxy-2-methylpyrimidine 8.7 kg of ethyl 3-(4-fluorophenyl)-3-oxopropionate, 11.7 kg of acetoamidine hydrochloride and 28.6 kg of potassium carbonate were stirred for 5 hours at about 50° C. in 34.5 kg of methanol. Insolubles were separated from the reaction mixture and washed with methanol, and the mother liquor and the washing were combined with water and neutralized with an 18% aqueous solution of hydrochloric acid. After neutralization, the crystal was ripened by stirring under reflux for 4 hours, and the precipitated crystal was isolated by centrifugation, washed with water, dried to obtain 7.4 kg of the target compound as a white crystal.

(Step 2)

Production of 4-chloro-6-(4-fluorophenyl)-2-methylpyrimidine 13.8 kg of 4-(4-fluorophenyl)-6-hydroxy-2-methylpyrimidine and 11.5 kg of phosphorus oxychloride were refluxed in acetonitrile, and stirred for 4 hours. The reaction solution was combined with water, and the precipitated crystal was separated, and the resultant crystal was washed and dried to obtain 14.6 kg of the target compound as a pale yellow crystal.

(Step 3)

Production of 4-(4-fluorophenyl)-2-methyl-6-(5-piperidinopentyloxy)pyrimidine 13.8 kg of 4-chloro-6-(4-fluorophenyl)-2-methylpyrimidine, 4.8 kg of 60% sodium hydride, 130 kg of cyclohexane and 10.6 kg of 5-piperidino-1-pentanol were stirred under reflux for 4 hours.

EXAMPLE 1

Production of 4-(4-fluorophenyl)-2-methyl-6-(5-piperidinopentyloxy)pyrimidine Hemihydrate The reaction solution obtained in Reference Example 1 was cooled, combined with 55 kg of water, stirred at room temperature for 1 hour, and then the aqueous layer was removed. The organic layer was extracted with a 3% aqueous solution of hydrochloric acid. The extract was neutralized with a 4% aqueous solution of sodium hydroxide, and the precipitated crystal was separated. The resultant crystal was subjected to an activated charcoal treatment in 120 kg of acetone, from which any insolubles were filtered off. The filtrate was combined with 85.2 kg of water to precipitate a crystal. The precipitated crystal was separated, and dried to obtain 19.2 kg (yield: 87%) of the target compound as a white crystal. The target compound thus obtained was identified microscopically or otherwise to have a crystallinity.

Melting point: 62.0 to 63.5° C.
Water content: 2.8%
% TG reduction: 2.5%
Elemental analysis: Calculated as $C_{21}H_{28}FN_3O \cdot \frac{1}{2}H_2O$:

| Theoretical | H: 7.98%, | C: 68.82%, | N: 11.47% |
| Found | H: 7.98%, | C: 68.86%, | N: 11.42% |

$^1$H NMR (200 MHz): δ 7.95–8.05(m, 2H), 7.09–7.21(m, 2H), 6.83(s, 1H), 4.38(t, J=13.2 Hz, 2H), 2.65(s, 3H), 2.27–2.38(Complex m, 6H), 1.74–1.88(m, 2H), 1.43–1.61 (Complex m, 10H)

EXAMPLE 2

Production of 4-(4-fluorophenyl)-2-methyl-6-(5-piperidinopentyloxy)pyrimidine Hemihydrate The solvent of the organic layer provided during the procedure similar to that in Example 1 was distilled off, and 16.0 g of the resultant oil was dissolved in 100 ml of a 3% aqueous solution of hydrochloric acid, to which then 80 ml of a 5% aqueous solution of sodium hydroxide was added, and the mixture was stirred at about 20° C. The precipitated crystal was recovered by filtration, washed with water and dried to obtain the target compound as a crystal.

EXAMPLE 3

Production of 4-(4-fluorophenyl)-2-methyl-6-(5-piperidinopentyloxy)pyrimidine Hemihydrate The solvent of the organic layer formed during the procedure similar to that in Example 1 was distilled off, and 153 g of the resultant oil was dissolved in 800 ml of cyclohexane, to which then 300 ml of water was added, and cyclohexane was distilled off under atmospheric pressure with stirring. And then the resultant mixture was cooled, and 700 ml of water was added. The precipitated crystal was recovered by filtration, and dried to obtain the target compound as a crystal.

EXAMPLE 4

Production of 4-(4-fluorophenyl)-2-methyl-6-(5-piperidinopentyloxy)pyrimidine Hemihydrate The solvent of the organic layer provided during the procedure similar to that in Example 1 was distilled off, and 207 g of the resultant oil was dissolved in a solvent mixture of about 600 ml of acetone and about 100 ml of water at 70° C., and then cooled to about 20° C. The precipitated crystal was recovered by filtration to obtain 167 g of the target compound as a crystal (yield: 77%).

EXAMPLE 5

Production of 4-(4-fluorophenyl)-2-methyl-6-(5-piperidinopentyloxy)pyrimidine Hydrochloride 18.0 kg of 4-(4-fluorophenyl)-2-methyl-6-(5-piperidinopentyloxy)pyrimidine hemihydrate obtained in Example 1 was dissolved in 142.2 kg of acetone, to which then 5.0 kg of hydrochloric acid was added and the mixture was stirred at about 20° C. for 1 hour. The precipitated crystal was separated, washed with acetone, and dried to obtain 17.4 kg of a crude crystal of the target compound. 17.0 kg of this crude crystal was recrystallized from ethanol to obtain 15.4 kg (yield: 91%) of the target compound as a white crystal. Purity: 99.9%.

HPLC Operation Conditions
Detector: UV Absorption spectrophotometer (measurement wavelength: 254 nm).
Column: Develosil ODS-HG-5/NOMURA KAGAKU, Inner diameter: 4.0 mm$\phi$, Length: 15 cm.
Column temperature: A constant temperature at about 40° C.
Mobile phase: 1.4 g of disodium hydrogen phosphate and 5.8 g of sodium lauryl sulfate were dissolved in a dilute phosphoric acid (1 in 1000) to make 1000 ml, a 250 ml aliquot of which was combined with 750 ml of methanol.

INDUSTRIAL APPLICABILITY

Since an inventive production method allows a highly pure acid salt of 4-(4-fluorophenyl)-2-methyl-6-(5-piperidinopentyloxy)pyrimidine to be produced readily at a high yield on a large scale without using a column chromatography by means of forming a hydrate of 4-(4-fluorophenyl)-2-methyl-6-(5-piperidinopentyloxy)pyrimidine followed by a conversion into the acid salt, it is suitable in an industrial production. Furthermore, an inventive hydrate has a sufficient stability during the production, and enables a production of highly pure Compound A, thus being extremely suitable in the production of Compound A.

What is claimed is:

1. A method for producing an acid salt of 4-(4-fluorophenyl)-2-methyl-6-(5-piperidinopentyloxy)pyrimidine comprising the steps of:
   (1) forming a hydrate of 4-(4-fluorophenyl)-2-methyl-6-(5-piperidinopentyloxy) pyrimidine,
   (2) isolating the hydrate and then
   (3) converting the hydrate into an acid salt.
2. The method according to claim 1 wherein the hydrate is a hemihydrate.
3. The production method according to claim 1 wherein the hydrate is a crystalline hemihydrate.
4. The method according to claim 1 wherein the acid salt is a hydrochloride.
5. The hemihydrate of 4-(4-fluorophenyl)-2-methyl-6-(5-piperidinopentyloxy)pyrimidine.
6. The hemihydrate according to claim 5, which is crystalline.
7. The method according to claim 1, wherein the step of forming the hydrate comprises:
   (1) dissolving 4-(4-fluorophenyl)-2-methyl-6-(5-piperidinopentyloxy)pyrimidine in an acidic aqueous solution and
   (2) adjusting the solution to a pH 7 or higher with a basic aqueous solution to form a hydrate of 4-(4-fluorophenyl)-2-methyl-6-(5piperidinopentyloxy)pyrimidine.
8. The method according to claim 1, wherein the step of forming the hydrate comprises:
   (1) dissolving 4-(4-fluorophenyl)-2-methyl-6-(5-piperidinopentyloxy)pyrimidine in an organic solvent and
   (2) distilling the solvent off in the presence of water followed by cooling to form a hydrate of 4-(4-fluorophenyl)-2-methyl-6-(5-piperidinopentyloxy)pyrimidine.
9. The method according to claim 1, wherein the step of forming the hydrate comprises the process of stirring 4-(4-fluorophenyl)-2-methyl-6-(5-piperidinopentyloxy)pyrimidine together with water or an aqueous organic solvent to form a hydrate of 4-(4-fluorophenyl)-2-methyl-6-(5-piperidinopentyloxy)pyrimidine.
10. The method according to claim 1, wherein the step of forming the hydrate comprises:
    (1) dissolving 4-(4-fluorophenyl)-2-methyl-6-(5 piperidinopentyloxy)pyrimidine in an acidic aqueous solution,
    (2) adjusting the solution to a pH 7 or higher with a basic aqueous solution to form a hydrate of 4-(4-fluorophenyl)-2-methyl-6-(5-piperidinopentyloxy)pyrimidine,
    (3) isolating the hydrate,
    (4) dissolving the hydrate in an aqueous organic solvent and
    (5) adding water to the solution to form a hydrate of 4-(4-fluorophenyl)-2-methyl-6-(5-piperidinopentyloxy)pyrimidine.
11. The method according to claim 1, wherein the step of forming the hydrate comprises:
    (1) dissolving 4-(4-fluorophenyl)-2-methyl-6-(5-piperidinopentyloxy)pyrimidine in an acidic aqueous solution,
    (2) distilling the solvent off in the presence of water followed by cooling to form a hydrate of 4-(4-fluorophenyl)-2-methyl-6-(5-piperidinopentyloxy)pyrimidine,
    (3) isolating the hydrate,
    (4) dissolving the hydrate in an aqueous organic solvent and (5) adding water to the solution to form a hydrate of 4-(4-fluorophenyl)-2-methyl-6-(5-piperidinopentyloxy)pyrimidine.

12. The method according to claim 10 or 11, wherein the aqueous organic solvent is a mixture of water and acetone.

13. The method according to any one of claims 7 to 11, wherein the hydrate is a hemihydrate.

14. The method according to any one of claims 7 to 11, wherein the hydrate is a crystalline hemihydrate.

* * * * *